United States Patent [19]

Boudakian

[11] Patent Number: 4,585,871
[45] Date of Patent: Apr. 29, 1986

[54] PROCESS FOR OXIDIZING HALOPYRIDINES TO HALOPYRIDINE-N-OXIDES

[75] Inventor: Max M. Boudakian, Pittsford, N.Y.

[73] Assignee: Olin Corporation, Cheshire, Conn.

[21] Appl. No.: 362,707

[22] Filed: Mar. 26, 1982

[51] Int. Cl.$^4$ .................................... C07D 213/18
[52] U.S. Cl. .................................................. 546/345
[58] Field of Search ........................................ 546/345

[56] References Cited

U.S. PATENT DOCUMENTS

| | | | |
|---|---|---|---|
| 2,686,786 | 8/1954 | Shaw et al. | 546/290 |
| 2,951,844 | 9/1960 | Shermer | 546/345 |
| 3,047,579 | 7/1962 | Witman | 546/152 |
| 3,203,957 | 8/1965 | Kirchner | 546/345 |
| 3,892,760 | 7/1975 | Hooks, Jr. et al. | 546/261 |
| 3,954,781 | 5/1976 | Hooks, Jr. et al. | 546/261 |
| 4,080,329 | 3/1978 | Muntwyler | 546/297 |

FOREIGN PATENT DOCUMENTS

| | | | |
|---|---|---|---|
| 0036638 | 9/1981 | European Pat. Off. | 71/94 |
| 847701 | 9/1960 | United Kingdom | 546/276 |

OTHER PUBLICATIONS

Abramovitch, Pyridine and Its Derivatives, Supplement Part Two, pp. 1–15, Wiley-Interscience Pub., QD 401 A3 C.2 (1974).
Kennedy et al., Journal of Organic Chemistry, vol. 25, pp. 1901–1906, Nov. 1960.
G. C. Finger and L. D. Starr, "Aromatic Fluorine Compounds. IX. 2-Fluoropyridines", J. Am. Chem. Soc., vol. 81, pp. 2674–2675 (Jun. 5, 1959).
R. F. Evans and H. C. Brown, J. Organic Chemistry, vol. 27, pp. 1329 et seq. (1962).
Katritzky, J. Chem. Soc., vol. 1957, pp. 191 et seq.
D. Sarantakis, J. K. Sutherland, C. Tortorella & V. Tortorella; "2 Fluoropyridine–N–Oxide in Peptide Chem.", Chem. Comm., No. 4, pp. 105–106, (1966).
R. J. Kennedy and A. M. Stock, "The Oxidation of Organic Substances by Potassium Peroxymonosulfate", J. of Organic Chem., vol. 25, 1901 (1960).

*Primary Examiner*—Alan L. Rotman
*Attorney, Agent, or Firm*—William A. Simons; Thomas P. O'Day

[57] ABSTRACT

Described is a process for oxidizing 2-chloropyridine or 2-bromopyridine to the corresponding N-oxide with peracetic acid generated in situ from $H_2O_2$ and acetic acid in the presence of a catalyst selected from the group consisting of sulfuric acid, alkali metal bisulfates, ammonium bisulfate, and mixtures thereof.

11 Claims, No Drawings

PROCESS FOR OXIDIZING HALOPYRIDINES TO HALOPYRIDINE-N-OXIDES

BACKGROUND OF THE INVENTION

1. Field of the Invention

The present invention relates to a process for making selected halopyridine-N-oxides by the oxidation of the corresponding halopyridine with peracetic acid generated in-situ. In particular, the present invention relates to a process for making 2-chloropyridine-N-oxide or 2-bromopyridine-N-oxide by the oxidation of the corresponding halopyridine with peracetic acid generated in-situ from acetic acid and $H_2O_2$ while in the presence of a catalyst selected from the group consisting of $H_2SO_4$, alkali metal bisulfates, ammonium bisulfate, and mixtures thereof.

2. Description of the Prior Art

2-Chloropyridine and 2-bromopyridine are chemical intermediates which may be converted to the sodium and zinc salts of pyridine-2-thiol-N-oxide. See U.S. Pat. Nos. 2,686,786 and 3,203,957, which issued to Shaw et al on Aug. 17, 1954, and Kirchner on Aug. 31, 1965, respectively. These compounds may also be converted to bis(2-pyridyl-1-oxide) disulfide. See U.S. Pat. Nos. 3,892,760 and 3,954,781, both of which issued to Hooks, Jr. anc Pitts on July 1, 1975, and May 4, 1976, respectively. All of these end products are excellent biocides and have been used in hair shampoos or skin cleansing preparations, or the like.

Because 2-chloropyridine-N-oxide is generally more economic to make, most of the work centered around improving its preparation. However, the procedures disclosed herein for making 2-chloropyridine-N-oxide may be practiced to convert 2-bromopyridine to its N-oxide with generally similar results.

In the past, 2-chloropyridine-N-oxide had been made from 2-chloropyridine by various methods. As shown in U.S. Pat. No. 2,951,844 which issued to Shermer on Sept. 6, 1960, 2-chloropyridine may be reacted with an aqueous peracetic acid solution in a mole ratio of 0.4 to 0.8 mole of peracetic acid per mole of 2-chloropyridine. The peracetic acid content of the aqueous solution may be preferably about 30 to 50 weight percent. This reaction may be shown by the following equation (A):

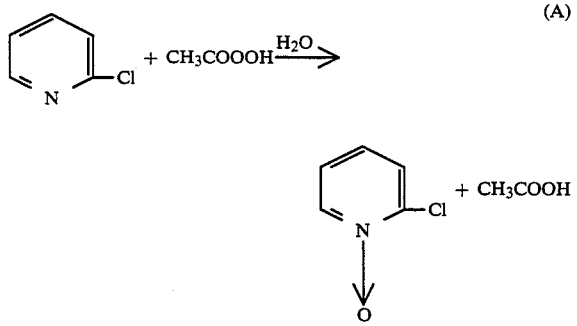

Upon reaction completion, the reaction mixture may be then neutralized with a base to a pH of 5 to 8, converting the acetic acid by-product to an acetate salt, for example, by using an aqueous NaOH solution. The unreacted 2-chloropyridine is recovered from the reaction mixture by distillation. Shermer teaches that a convenient method for preparing the peracetic acid comprises mixing 70 parts by weight of glacial acetic acid with 30 parts by weight of $H_2O_2$ in the presence of one part of sulfuric acid. The resulting mixture contains about 40% peracetic acid, 40% acetic acid, 15% water, and 5% $H_2O_2$ (with less than 1% $H_2SO_4$). See Col. 2, lines 5-11 of this patent.

This "Preformed Peracetic Acid Oxidation Route" as taught by Shermer has several disadvantages. Peracetic acid is relatively unstable which makes its storage a problem. Also, there are a limited number of suppliers which may make it relatively expensive. Further, since excess 2-chloropyridine is used as a starting material, low batch productivity results and greater reactor volumes are needed. Still further, because more total acid is used, more base is needed for neutralization and the effluent from the process will have a high biological oxygen demand (BOD).

Finger and Starr in "Aromatic Fluorine Compounds. IX.2-Fluoropyridines", *J. Am. Chem. Soc., Vol.* 81, pages 2674 and 2675 (1959) teach another "Preformed Peracetic Acid Oxidation Route". They reacted 2-chloropyridine with a commercial 40% by weight peracetic acid solution in the presence of extra acetic acid. The mole ratio of 2-chloropyridine to total acid was 1:6.9. This high molar ratio has the same disadvantages of Shermer, but, more so.

In U.S. Pat. No. 3,203,957, which issued to Kirchner on Aug. 31, 1965, 2-chloropyridine-N-oxide is made by oxidizing 2-chloropyridine with $H_2O_2$ and maleic or phthalic anhydride at a temperature in the range from 30° C. to about 90° C. The mole ratio of $H_2O_2$ to 2-chloropyridine may be from 0.5:1 to 1.2:1 and the mole mole ratio of maleic or phthalic anhydride to $H_2O_2$ is at least 1:1. The reaction may be preferably carried out in the presence of an inert solvent simply for the purpose of facilitating physical handling of the reaction mixture. Kirchner also teaches that the reaction involves the in situ formation of monoperoxymaleic or monoperoxyphthalic acid.

This "Monoperoxy-Maleic or Phthalic Anhydride Oxidation Route" also has several disadvantages. First, the maleic and phthalic anhydride reactants are relatively more expensiVe that acetic acid. Also, the presence of the by-product sodium maleate or sodium phthalate after neutralization sometimes presents problems in making later end products.

For practical purposes, the process taught by Kirchner requires an inert solvent or excess 2-chloropyridine. The use of an inert solvent or excess 2-chlorpyridine contributes to lower batch productivity and the use of the former also may require a separation step. Furthermore, the use of maleic or phthalic anhydride as reactants may create greater environmental problems than when comparable amounts of acetic acid are used because of their greater molecular weights.

Besides the above-noted patented methods for making 2-chloropyridine-N-oxide, other processes have been described in the literature. R. F. Evans and H. C. Brown [*J. Org. Chem.*, 27, 1329 (1962)] taught that 2-chloropyridine-N-oxide may be prepared by reacting 2-chloropyridine with glacial acetic acid and $H_2O_2$ at 70°-80° C. for about 12 hours *without* the use of any catalyst. However, they employed an acetic acid to 2-chloropyridine mole ratio of about 10.5:1. Katritzky [*J. Chem. Soc.*, 191 (1957)] also describes the making of 2-chloropyridine-N-oxide by reacting 2-chloropyridine with acetic acid and aqueous $H_2O_2$ without any catalyst overnight at 80° C. Again, he employed an acetic acid to 2-chloropyridine mole ratio of about 13.2:1. The use of these exhorbitant molar quantities of acetic acid and long reaction times does result in low batch productivity; require large amounts of NaOH for neutralization; and result in a high BOD in the waste water effluent from the process. This non-catalytic in situ technique is only of academic interest and has imited practical application.

Work was also carried out wherein 2-chloropyridine was oxidized with peracetic acid formed in situ by the reaction of acetic acid and $H_2O_2$ in the presence of an acid cation exchange resin catalyst (i.e., a sulfonated copolymer of styrene and 8% divinyl-benzene). See Example VI of U.S. Pat. No. 3,203,957, which issued to Kirchner. The patent admits this technique for oxidizing 2-chloropyridine to 2-chloropyridine-N-oxide was inferior. It should be noted that this reaction resulted in the low consumption of $H_2O_2$ (74.6%). This means the reaction rate will be relatively slow and methods for disposing the unreacted $H_2O_2$ must be employed.

Non-published work has been carried out at Olin Corporation for making 2-chloropyridine-N-oxide by reacting 2-chloropyridine with acetic acid and $H_2O_2$ in the presence of very small amounts of $H_2SO_4$ (0.02 mole of $H_2SO_4$ per 1.0 mole of 2-chloropyridine reactant). Furthermore, this work employed an excess of 2-chloropyridine over $H_2O_2$ (1.0 mole: 0.6 mole). It should be noted that this work also resulted in the low consumption of $H_2O_2$ (57%). The excess 2-chloropyridine contributed to low batch productivity.

In U.S. Pat. No. 3,047,579, which issued to Witman on July 31, 1962, 2-chloropyridine may be oxidized with $H_2O_2$ to 2-chloropyridine-N-oxide in the presence of "unstable inorganic per-compounds of the acid-forming elements of groups VA, VIA, VIB, and VIII" of the periodic table (e.g., pertungstic acid) as catalysts. Witman also teaches that this type of catalyzed reaction may be most effectively carried out in a liquid phase reaction medium, using a lower aliphatic monocarboxylic acid such as glacial acetic acid. See Col. 5, line 44 to Col. 6, line 5 of this patent.

This "Tungsten Catalyzed Oxidation Route" also has some disadvantages. While higher batch productivity may be more consistently achieved than in the above-discussed preformed peracetic acid route, the expensive tungsten catalyst must be recovered from the reaction mixture for economic reasons. However, there may be some carry-over of the tungsten with the 2-chloropyridine-N-oxide product. This carry-over which is extremely difficult to prevent, may result in undesirably colored sodium or zinc salts of pyridine-2-thiol-N-oxide later made from this product.

In all, the conversion and selectivity of 2-chloropyridine to 2-chloropyridine-N-oxide with some of these prior art processes have not been appreciably high, especially in large-scale production modes. Therefore, there is a need to raise the conversion and selectivity of this reaction and similar reactions to lower the costs of producing the N-oxide products and products derived from them. Furthermore, the production of zinc pyridine-2-thiol-N-oxide from 2-chlorpyridine-N-oxide produced by these prior art processes has sometimes been associated with serious color problems (i.e., this zinc salt has been too dark) which prevent it from being used in certain shampoo formulations. As stated above, it is believed that these color problems are caused by the presence of by-products of the desired N-oxide product. Thus, there is also a need to produce N-oxide products which do not have an appreciable amount of by-products which effect undesirable colors to final products. Furthermore, as can be seen from the discussion above, higher batch productivity and reduced organic effluents are desired. The present invention presents a solution to all of these needs.

BRIEF SUMMARY OF THE INVENTION

Accordingly, the present invention is directed to a process for oxidizing 2-chloropyridine or 2-bromopyridine to the corresponding N-oxide with peracetic acid generated in situ from $H_2O_2$ and acetic acid comprising
reacting at a temperature from about 30° C. to about 120° C. (a) hydrogen peroxide, (b) a 2-halopyridine selected from the group consisting of 2-chloropyridine and 2-bromopyridine, and (c) acetic acid in the presence of a catalyst selected from the group consisting of sulfuric acid, alkali metal bisulfates, ammonium bisulfate, and mixtures thereof, in order to make the corresponding 2-halopyridine-N-oxide; this reaction carried out by employing from about 0.5 to about 5.0 moles of $H_2O_2$ per mole of 2-halopyridine; employing from about 0.5 to about 3.0 moles of acetic acid per mole of 2-halopyridine and employing from about 0.08 to about 0.8 mole of catalyst per mole of 2-halopyridine.

DETAILED DESCRIPTION

The present invention is an improvement over the above-discussed methods for making 2-halopyridines. Specifically, this invention is characterized by the use of peracetic acid as an oxidizing agent for converting a 2-halopyridine to a 2-halopyridine-N-oxide. The peracetic acid is generated in situ (i.e., formed and used in the presence of the 2-halopyridine) from $H_2O_2$ and acetic acid in the presence of certain amounts of selected catalysts. The process of this invention may be illustrated by the following equation (B) wherein 2-chloropyridine is utilized:

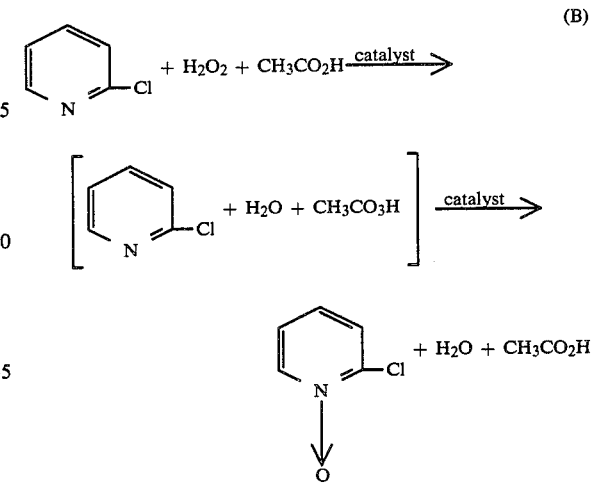

The 2-halopyridine reactants of the present invention may be either 2-chloropyridine or 2-bromopyridine. Both of these compounds are well known and they may be made by many conventional methods. Because of cost considerations, 2-chloropyridine is favored over 2-bromopyridine as a chemical intermediate.

The acetic acid reactant is also a well known and widely available commercial product. For purposes of this invention, 100% by weight glacial acetic acid solutions are preferred. Aqueous solutions (down to 50% by weight acetic acid) of acetic acid may be employed. The use of $H_2O$ in the reaction mixture is not critical. The use of some water may be beneficial since it could work as a heat transfer agent and increase the rate of reaction. Of course, the use of too much water will increase the reaction volume and thus decrease the batch efficiency.

The third reactant, $H_2O_2$, of the present invention is also a widely available commercial product. It is generally available in aqueous solutions containing from about 3% to about 90% by weight $H_2O_2$. Because there are severe handling problems (e.g., possibility of explosions) at the very high concentrations and low productivity at the very low concentrations, it is preferred to employ $H_2O_2$ in aqueous solutions containing about 30% to about 70% by weight $H_2O_2$.

A critical feature of the present invention is carrying out the in situ generation of peracetic acid and the reaction to the corresponding N-oxide in the presence of certain amounts of selected catalysts. These catalysts may be $H_2SO_4$, alkali metal bisulfates, ammonium bisulfate, or mixtures thereof. Hydrate salts of the bisulfates are included too. Sodium and potassium bisulfate ($NaHSO_4$ and $KHSO_4$) are the preferred alkali metal bisulfates. The choice of these catalysts makes the present process very flexible. If a liquid reaction mixture and catalyst are preferred, concentrated $H_2SO_4$ or more dilute aqueous solutions are more desirable. If a solid catalyst is desired so that it may be recycled, the bisulfates, especially sodium and potassium bisulfate, are preferred.

When $H_2SO_4$ is employed as the catalyst, the reaction mechanism is believed to go through an active oxidizing intermediate comprised of either peracetic acid or a synergistic combination of peracetic acid and peroxymonosulfuric acid (Caro's Acid, $H_2SO_5$). When an alkali metal bisulfate is employed as the catalyst, the active oxidizing intermediate is believed to be either peracetic acid or a synergistic combination of peracetic acid and an alkali metal monopersulfate ($MHSO_5$). In either case, the use of in situ generated peracetic acid is different from pre-formed peracetic acid in that the former is formed instantly and used instantly. However, the present invention is not limited to any particular reaction mechanism, but only to those reaction parameters stated to be critical.

The amount of catalyst is also critical to this invention. As can be seen by the Examples and Comparisons shown below, this oxidation reaction ignificantly decreases with the absence of these catalysts. Likewise, the use of too much catalyst will interfere with the reaction and cause selectivity of the reaction to drop. It has been found that the amount of catalyst beneficial for running this oxidation reaction at a suitable rate is from about 0.08 to about 0.8 preferably from 0.1 to about 0.6, moles of total catalyst per mole.

The mole ratio of $H_2O_2$ to 2-halopyridine should be from about 0.5:1 to about 5:1; preferably from about 0.75:1 to about 2.5:1. The mole ratio of acetic acid to 2-halopyridine should be from about 0.5:1 to 3:1; preferably from about 0.75:1 to about 2:1. The employment of amounts of $H_2O_2$ and acetic acid below these mole ratios may cause a drop in product yields and above these mole ratios will decrease batch efficiency.

The reaction temperature should be from about 30° C. to about 120° C.; preferably, from about 60° C. to about 85° C. Temperatures below about 30° C. may result in too slow a reaction to be commercially feasible and temperatures above about 120° C. may cause uncontrollable reaction rate and side reactions. The reaction should be given sufficient time (e.g., from about 1 hour to 8 hours) to go to completion. After the reaction appears complete or at any desired time, the 2-halopyridine may be recovered from the reaction mixture by suitable means or may be used while in the reaction mixture to make further chemical products.

It is preferable to operate at atmospheric pressure but lower or higher pressures may be used if desired, for example, 0.75 to 5 atmospheres.

Depending upon the specific method by which the reactants are added to the reaction mixture, the time for completion of the reaction will vary with the reaction temperature and/or the speed at which the reactants are combined. The reaction time will decrease when the addition is speeded up or with an increase in temperature.

The in situ generation of peracetic acid may be carried out in different ways. One preferred method is to simply combine $H_2O_2$, acetic acid, and the 2-halopyridine with the catalyst at room temperature (e.g., about 25° C.) and then raise the temperature of the reaction mixture to the desired temperature. Another preferred method is to combine acetic acid and the 2-halopyridine with the catalyst at room temperature, raise the temperature of this mixture to the desired temperature, and then add the $H_2O_2$ in incremental amounts.

Any suitable method for recovering the 2-halopyridine-N-oxide product from the reaction mixture may be employed. One preferred method is to neutralize the reaction mixture with a base (e.g., NaOH) followed by steam distillation under vacuum to remove the unreacted 2-halopyridine.

2-Chloropyridine-N-oxide or 2-bromopyridine-N-oxide made according to the process of this invention may be converted into sodium pyridine-2-thiol-N-oxide by a mercaptization step in which NaSH or $Na_2S$ in the presence of NaOH are reacted with the N-oxide compound. This conversion is described in U.S. Pat. No. 3,159,640, which issued to McClure and Shermer on Dec. 1, 1964.

Zinc pyridine-2-thiol-N-oxide may be made from the sodium pyridine-2-thiol-N-oxide by reacting the latter with a zinc salt (e.g., $ZnSO_4$ or $ZnCl_2$). See U.S. Pat. No. 4,080,329, which issued to Muntwyler on Mar. 21, 1979.

Besides 2-chloropyridine-N-oxide and 2-bromopyridine-N-oxide, the process of the present invention also contemplates the making of other halopyridine-N-oxides, including 2-fluoropyridine-N-oxide; 2-iodopyridine-N-oxide; corresponding 3- and 4-halopyridine-N-oxides; 2,3-, 2,4-, 2,5-, 2,6-, and 3,5-dihalopyridine-N-oxides; and alkyl-substituted halopyridine-N-oxides such as 2-chloro-3-picoline-N-oxide, 2-chloro-4-picoline-N-oxide, 6-chloro-3-picoline-N-oxide, 6-chloro-2-picoline-N-oxide, and 6-chloro-2,4-lutidine-N-oxide.

The following Examples and Comparisons are given to further illustrate the present invention. All parts and percentages are by weight unless explicitly stated otherwise.

USE OF $H_2SO_4$ AS CATALYST

The following three examples use $H_2SO_4$ as a catalyst in amounts equal to 0.12 mole, 0.3 mole, and 0.6 mole, respectively, per mole of 2-chloropyridine (2-PCl) reactant. These examples illustrate the beneficial effects resulting from using certain amounts of this liquid catalyst.

EXAMPLES 1-3

Three mixtures each consisting of acetic acid (1.2 moles; wt. 72.0 gm), sulfuric acid (either 0.12, 0.3, or 0.6 moles; 14.7 gm, 29.4 gm, or 44.1 gm; corresponding to 4.2, 10.4, and 20.8% by wt. of total oxidation mixtures, respectively) 2-chloropyridine (2-PCl) (1.0 mole; 113.6 gm, and 50% aqueous solution of $H_2O_2$ (1.0 mole; 68.0 gm) were heated to 70° C. for 3 hours. The solutions were each neutralized to a pH of 7.1 with an aqueous solution of 20% by weight NaOH and the unreacted 2-chloropyridine was then isolated by vacuum azeotropic distillation (50° C./50 mm). $H_2O_2$ consumptions were measured by titration. 2-Chloropyridine-N-oxide contents in the distillation pot liquors were measured by standard reductometric techniques. The results of these experiments are given in Table I.

corresponding to 0.319 mole (62.8% selectivity to the N-oxide).

USE OF NO CATALYST

The following two Comparisons use no $H_2SO_4$ or $NaHSO_4$ catalyst. These illustrate the adverse effects of using no catalyst.

COMPARISON 1

A mixture consisting of acetic acid (1.2 moles; 72 gm), 2-chloropyridine (1.0 mole; 113.6 gm), water (85 ml), and 50% hydrogen peroxide (68.0 gm; 1.0 mole) was heated to 70° C. for 3 hours. The solution was neutralized to pH 7.1 with 20% sodium hydroxide and 2-chloropyridine steam distilled at 50° C./50 mm (wt. 100.2 gm, dry basis; 0.882 mole recovered or 11.8% 2-chloropyridine conversion).

Assay of an aliquot of the steam distillation pot liquor disclosed only 20% consumption of hydrogen peroxide.

TABLE I

| | Use of $H_2SO_4$ As Catalyst | | | | | 2-PCl-N—Oxide | |
|---|---|---|---|---|---|---|---|
| Comparison or Example | $H_2SO_4$:2-PCl Mole Ratio | $H_2O_2$:2-PCl Mole Ratio | $CH_3CO_2H$:2-PCl Mole Ratio | % $H_2O_2$ Consumption | % 2-PCl Conversion | Uncorr. Yield | Selectivity |
| C-2 | 0:1 | 1:1 | 1.2:1 | 15.6 | 23.8 | 4.5 | 49.2 |
| 1 | 0.12:1 | 1:1 | 1.2:1 | 96.1 | 54.3 | 42.3 | 77.9 |
| 2 | 0.3:1 | 1:1 | 1.2:1 | 97.4 | 44.5 | 42.5 | 95.5 |
| 3 | 0.6:1 | 1:1 | 1.2:1 | 99.0 | 43.3 | 36.3 | 83.9 |

USE OF NAHSO4 CATALYST

The following example uses a sodium bisulfate catalyst in an amount equal to 0.3 mole per mole of 2-chloropyridine reactant. This example illustrates the beneficial results from using this solid catalyst.

EXAMPLE 4

A mixture consisting of acetic acid (1.2 moles; 72.0 gm), sodium bisulfate (anhydrous) (0.3 mole; 35.4 gm), 2-chloropyridine (1.0 mole; 113.6 gm), and 50% hydrogen peroxide (1.0 mole; 68.0 gm) was heated to 70° C. for 3 hours. The solution was neutralized to pH 7.1 with 20% sodium hydroxide and unreacted 2-chloropyridine steam distilled (50° C./50 mm) (wt. 63.05 gm, dry basis, 0.555 mole recovered or 44.5% 2-chloropyridine conversion). Titration of the steam distillation liquor established 97.4% of the hydrogen peroxide had been consumed.

The steam distillation pot liquor (wt. 705.5 gm) assayed 7.80% 2-chloropyridine-N-oxide corresponding to 0.425 mole (95.5% selectivity to 2-chloropyridine-N-oxide).

EXAMPLE 4A

The procedure of Example 4 was repeated except that 0.6 moles (70.8 gm) of sodium bisulfate catalyst was employed. Titration with 0.1N $KMnO_4$ indicated complete $H_2O_2$ consumption.

The acidic oxidation liquor (wt. 225.6 gm) was decanted, neutralized to pH 7.1 with 17% NaOH (336 gm) and unreacted 2-chloropyridine steam stilled at 50° C./50 mm (wt. 55.7 gm, dry basis; 0.491 mole recovered or 50.9% conversion). The steam distillation pot liquor (wt. 445.1 gm) assayed 9.3% 2-chloropyridine-N-oxide This liquor (wt. 522.5 gm), after treatment with $MnO_2$ to destroy excess $H_2O_2$, assayed 2.0% 2-chloropyridine-N-oxide, corresponding to 0.081 mole (68.6% selectivity).

COMPARISON 2

An identical experiment was conducted in the absence of $H_2SO_4$ or $NaHSO_4$ catalyst and also excluded water. Again the amount of hydrogen peroxide consumption was low (15.6%). Recovery of 2-chloropyridine disclosed 86.6 gm (dry basis, 0.762 mole or 23.8% conversion). However, assay of the steam distillation liquor (wt. 336.0 gm) showed 4.5% 2-chloropyridine-N-oxide, corresponding to only 0.117 mole (49.2% selectivity to 2-chloropyridine-N-oxide). Comparison of the results of this experiment with Examples 1-3 is shown in Table I.

CRITICAL ROLE OF ACETIC ACID REACTANT

The following Example 5 (together with Example 2) and Comparisons 3 and 4 illustrate the importance of employing selected amounts of acetic acid with an $H_2SO_4$ catalyst.

EXAMPLE 5

The procedure of Example 2 was repeated except 2.4 moles of acetic acid (instead of 1.2 moles) were used per one mole of 2-chloropyridine. The results are given in Table II.

COMPARISONS 3 AND 4

The procedure of Example 2 was again repeated except no moles or 0.12 moles of acetic acid were used. The results are also shown in Table II. Comparing the results of Examples 2 and 5 with Comparisons 3 and 4, as shown in Table II, clearly shows the importance of having minimum amounts of acetic acid in the reaction mixture.

TABLE II

Varying Acetic Acid Amounts in $H_2SO_4$ Catalyst System

| Example or Comparison | $H_2SO_4$:2-PCl Mole Ratio | $H_2O_2$:2-PCl Mole Ratio | $CH_3CO_2H$:2-PCl Mole Ratio | % $H_2O_2$ Consumption | % 2-PCl Conversion | 2-PCl-N—Oxide Uncorr. Yield | 2-PCl-N—Oxide Selectivity |
|---|---|---|---|---|---|---|---|
| E-5 | 0.3:1 | 1:1 | 2.4:1 | 98.4 | 49.4 | 43.2 | 87.4 |
| E-2 | 0.3:1 | 1:1 | 1.2:1 | 97.4 | 44.5 | 42.5 | 95.5 |
| C-4 | 0.3:1 | 1:1 | 0.12:1 | 65.0 | 31.1 | 21.4 | 68.7 |
| C-3 | 0.3:1 | 1:1 | 0:1 | 19.2 | 10.4 | 11.5 | 111.7 |

The following Comparisons (when compared to Example 4) illustrate the importance of employing selected amounts of acetic acid with an $NaHSO_4$ catalyst.

EXAMPLE WITH NO ACETIC ACID

Comparison 5

A mixture consisting of 2-chloropyridine (1.0 mole; 113.6 gm), sodium bisulfate monohydrate (0.3 mole; 47.2 gm), water (85 ml), and 50% hydrogen peroxide (1.0 mole; 68 gm) was heated to 70° C. for 3 hours. The solution was neutralized to pH 7.1 with 20% sodium hydroxide. (Titration of 0.1 N $KMnO_4$ found 40.5% $H_2O_2$ consumption.) Steam distillation (50° C./50 mm) gave 2-chloropyridine (wt. 100.4 gm, dry basis; 0.884 mole recovered or 11.6% conversion of 2-chloropyridine).

The steam distillation pot liquor (wt. 739 gm) assayed 1.69% 2-chloropyridine-N-oxide (after $MnO_2$ treatment to destroy excess $H_2O_2$), corresponding to 0.096 mole (82.8% selectivity to 2-chloropyridine-N-oxide).

EXAMPLE WITH 0.12 MOLE ACETIC ACID

Comparison 6

A mixture consisting of 2-chloropyridine (1.0 mole; 113.6 gm), anhydrous sodium bisulfate (0.3 mole; 35.4 gm), acetic acid (0.12 mole; 7.2 gm), and 50% hydroxide (1.0 mole; 68 gm) was heated to 70° C for 3 hours. The solution was neutralized to pH 7.1 with 20% sodium hydroxide. Steam distillation (50° C./50 mm) gave 2-chloropyridine (wt. 90.7 gm, dry basis; 0.782 mole recovered or 21.8% conversion of 2-chloropyridine).

Assay of the steam distillation liquor indicated only 34.5% $H_2O_2$ consumption.

Assay of the steam distillation liquor (201.4 gm) showed 12.2% 2-chloropyridine-N-oxide (after treatment with $MnO_2$), corresponding to 0.19 mole (87.2% selectivity to 2-chloropyridine-N-oxide).

CHANGES IN $H_2O_2$ STOICHIOMETRY

The following Examples 6 and 7 (together with Example 2) illustrate the effects of changing the molar ratio of $H_2O_2$ to 2-chloropyridine (2-PCl) in the reaction mixture containing the $H_2SO_4$ catalyst. The following Examples 8 and 9 (together with Example 4) illustrate the effects of changing the molar ratio of $H_2O_2$ to 2-PCl in the reaction mixture containing the $NaHSO_4$ catalyst.

EXAMPLES 6 AND 7

The procedure set forth for Example 2 was repeated except that the mole ratio of $H_2O_2$:2-PCl was changed from 1:1 to either 0.6:1 or 1.5:1 (the acetic acid to 2-PCl mole ratio was also slightly increased in the 0.6:1 experiment). The results of these Examples are given in Table III.

TABLE III

Varying the $H_2O_2$:2-PCl Mole Ratio in $H_2SO_4$ Catalyst System

| Example | $H_2SO_4$:2-PCl Mole Ratio | $H_2O_2$:2-PCl Mole Ratio | $CH_3CO_2H$:2-PCl Mole Ratio | % $H_2O_2$ Consumption | % 2-PCl Conversion | 2-PCl-N—Oxide Uncorr. Yield | 2-PCl-N—Oxide Selectivity |
|---|---|---|---|---|---|---|---|
| 6 | 0.3:1 | 0.6:1 | 1.33:1 | 99.3 | 33.0 | 26.4 | 80.0 |
| 2 | 0.3:1 | 1:1 | 1.2:1 | 97.4 | 44.6 | 42.6 | 95.5 |
| 7 | 0.3:1 | 1.5:1 | 1.2:1 | 97.5 | 58.4 | 51.2 | 87.7 |

EXAMPLE 8

0.5 $H_2O_2$/1.0 2-PCl Stoichiometry

A mixture consisting of acetic acid (1.2 moles; 72 gm), anhydrous sodium bisulfate (0.3 mole; 35.4 gm), 2-chloropyridine (1.0 mole; 113.6 gm), and 50% hydrogen peroxide (0.5 mole; 34 gm) was heated to 80° C. for 2 hours. The solution was neutralized to pH 7.1 with 20% sodium hydroxide. (Titration with 0.1 N $KMnO_4$/sulfuric acid showed complete hydrogen peroxide consumption.)

Steam distillation (50° C./50 mm) provided unreacted 2-chloropyridine (83.4 gm, dry basis; 0.735 mole recovered or 26.5% 2-chloropyridine conversion).

Assay of the pot liquor (wt. 499.7 gm) showed 5.7% 2-chloropyridine-N-oxide, corresponding to 0.220 mole (83% selectivity to 2-chloropyridine-N-oxide).

EXAMPLE 9

1.5 $H_2O_2$/1.0 2-PCl Stoichiometry

A mixture consisting of acetic acid (1.2 moles, 72 gm) anhydrous sodium bisulfate (0.3 mole; 35.4 gm), 2-chloropyridine (1.0 mole, 113 6 gm), and 50% hydrogen peroxide (1.5 moles, 102 gm) was heated to 70° C. for 3 hours. The solution was neutralized to pH 7.1 with 20% sodium hydroxide.

2-Chloropyridine was steam distilled (50° C./50 mm) to give 48.9 gm (dry basis; 0.43 mole, corresponding to 57% conversion of 2-chloropyridine). Titration of the steam distillation liquor indicated 80.7% hydrogen peroxide consumption. Assay of this liquor, wt. 518.8 gm, (after $MnO_2$ treatment) indicated 13.76% 2-chloropyridine-N-oxide, corresponding to 0.552 mole (96.8% selectivity to 2-chloropyridine-N-oxide).

ALTERNATIVE $H_2O_2$ ADDITION

All of the above examples and comparisons employed a "cold-slug" $H_2O_2$ feed technique. That addition method involved adding the $H_2O_2$ with the other reactants and catalyst at room temperature and then increasing the reaction temperature to the desired temperature. The following Examples 10 and 11 illustrate an alternative $H_2O_2$ feeding method wherein that reactant is added to the reaction mixture at the desired reaction temperature in incremental amounts.

EXAMPLE 10

A mixture consisting of 2-chloropyridine (1.0 mole; 113.6 gm), sulfuric acid (0.3 mole; 29 gm) and glacial acetic acid (1.2 moles; 72 gm) was heated to 70° C. 50% Hydrogen peroxide (1.5 moles; 102.0 gm) was added over a 2 hour period. The oxidation mixture was held at 70° C. For an additional hour. Assay of the oxidation liquor indicated 90.9% of the charge dhydrogen peroxide had been consumed.

The solution was neutralized to pH 7.1 with 20% sodium hydroxide and unreacted 2-chloropyridine recovered by steam distillation at 50° C./50 mm. A total of 48.9 gm (0.430 mole, dry basis) of 2-chloropyridine corresponding to 57.0% conversion was realized.

The steam distillation pot liquor (wt. 634.2 gm) was treated with $MnSO_4$ to destroy residual $H_2O_2$ (3.6 gm or 7.1% of the initial charge). Titration by the standard reductometric method showed 10.74% 2-chloropyridine-N-oxide, corresponding to 0.526 mole (92.2% selectivity to 2-chloropyridine-N-oxide).

EXAMPLE 11

A mixture consisting of 2-chloropyridine (5.0 moles; 568 gm), sodium bisulfate (anhydrous; 5 moles; 180.1 gm), and glacial acetic acid (6.0 moles; 360 gm) was heated to 70° C. 50% Hydrogen peroxide (5.0 moles; 340.1 gm) was added over a 3 hour period. The oxidation mixture was then held at 70° C. for an additional 2.5 hours. Assay of the oxidation liquor indicated that 95.7% of the hydrogen peroxide had been consumed.

The solution was neutralized to pH 7.1 with 20% sodium hydroxide and unreacted 2-chloropyridine recovered by steam distillation at 50° C./50 mm. A total of 3.163 moles (359.3 gm) 2-chloropyridine (dry basis, corresponding to 36.7% conversion) was recovered.

Assay of the steam distillation pot liquor (wt. 2987 gm) was 6.77% 2-chloropyridine-N-oxide, corresponding to 1 561 moles (85.0% selectivity to 2-chloropyridine-N-oxide).

PREPARATION OF SODIUM AND ZINC PYRIDINE-2-THIOL-N-OXIDE

The following Examples 12 and 13 illustrates that sodium and zinc pyridine-2-thio-N-oxide may be made from the 2-chloropyridine-N-oxide made by the methods given in Example 2 (with $H_2SO_4$ catalyst) in Example 4 (with $NaHSO_4$ catalyst).

EXAMPLE 12

A. Preparation of Sodium Pyridine-2-thiol-N-oxide

A solution consisting of 20% sodium hydroxide (47.5 gm; 0.238 mole), sodium hydrosulfide (22.4 gm; 72% concentration as hydrate; 0.288 mole), and water (62.5 gm) was added to a 333.6 gm aliquot of a solution of 2-chloropyridine-N-oxide made according to the method set forth in Example 2 above (0.250 mole, dry basis; 9.72% concentration) at 22° C. (0.25 hour addition period). The mercaptization mixture was heated to 75°–80° C. (2 hours). The solution was cooled to 55° C. and 32% hydrochloric acid added (to pH 6.5); a nitrogen sub-surface purge removed liberated hydrogen sulfide.

The acidified mercaptization mixture was filtered. The filtrate (wt. 445.8 gm) assayed 7.4% sodium pyridine-2-thiol-N-oxide [wt. (g), dry basis, 31.7 gm; 0.212 mole or 84.8% yield].

B. Preparation of Zinc Pyridine-2-thiol-N-oxide

To a 419.9 gm aliquot of the above solution of sodium pyridine-2-thiol-N-oxide (29.9 gm dry basis; 0.200 mole) was added a solution of zinc sulfate (20.0 gm, 52.5% concentration as hydrate; 0.111 mole) and water (80 gm) at room temperature. After 0.5 hour agitation, zinc pyridine-2-thiol-N-oxide was filtered and washed with water. The wet cake (60.2 gm) was dried to constant weight (33.8 gm; 0.107 mole or 100% yield; 97.1% assay). The zinc pyridine-2-thiol-N-oxide had the following color designation: L, 92.0; a, −3.5; b, 4.9. (Hunterlab Tristimulus Colorimeter, Model D25A-2, Reston, Va. 22090).

EXAMPLE 13

A. Preparation of Sodium Pyridine-2-thiol-N-Oxide

A solution consisting of 20% sodium hydroxide (47.5 gm; 0.238 mole), sodium hydrosulfide (22.4 gm; 72% concentration as hydrate; 0.288 mole), and water (62.5 gm) was added to a 415 gm aliquot of a solution of 2-chloropyridine-N-oxide made according to a method substantially the same as Example 4 above (0.250 mole, dry basis; 7.8% concentration) at 23° C. (0.25 hour period). The mercaptization mixture was heated to 75°–80° C. (2 hours). The solution was cooled to 55° C. and 32% hydrochloric acid added (to pH 6.5); a nitrogen sub-surface purge removed liberated hydrogen sulfide.

The acidified mercaptization mixture was filtered. The filtrate (wt. 539.7 gm) assayed 6.0% sodium pyridine-2-thiol-N-oxide [wt. (gm), dry basis, 32.4 gm; 0.217 mole or 86.8% yield].

B. Preparation of Zinc Pyridine-2-thiol-N-Oxide

To a 514.8 gm aliquot of the above solution of sodium pyridine-2-thiol-N-oxide (30.9 gm dry basis; 0.207 mole) was added a solution of zinc sulfate (20.3 gm; 52.5% concentration as hydrate; 0.113 mole), and water (81 gm) at room temperature. After 0.5 hour agitation, insoluble zinc pyridine-2-thiol-N-oxide was filtered and washed with water. The wet cake (59.9 gm) was dried to constant weight (33.8 gm; 0.107 mole or 85.2% yield; 96.1% assay). The zinc pyridine-2-thiol-N-oxide had the following color designation: L, 93.0; a, −3.7; b, 5.2. (Hunterlab Tristimulus Colorimeter, Model D25A-2, Reston, Va. 22090).

What is claimed is:

1. A method of producing a 2-halopyridine-N-oxide comprising
    reacting at a temperature from about 30° C. to about 120° C. (a) hydrogen peroxide, (b) a 2-halopyridine selected from the group consisting of 2-chloropyridine and 2-bromopyridine, and (c) acetic acid in the presence of a catalyst selected from the group consisting of alkali metal bisulfate, ammonium bisulfate, and mixtures thereof, in order to produce the corresponding 2-halopyridine-N-oxide; said reaction carried out by employing from about 0.5 to about 5.0 moles of $H_2O_2$ per mole of 2-halopyridine; employing from about 0.5 to about 3.0 moles of acetic acid per mole of 2-halopyridine, and employing from about 0.08 to about 0.8 moles of catalyst per mole of 2-halopyridine.

2. The method of claim 1 wherein said halopyridine is 2-chloropyridine.

3. The method of claim 1 wherein said catalyst is an alkali metal bisulfate selected from the group consisting of sodium bisulfate and potassium bisulfate.

4. The method of claim 1 wherein about 0.75 to about 2.5 moles of $H_2O_2$ are employed per mole of 2-halopyridine.

5. The method of claim 1 wherein said $H_2O_2$ is employed in the form of an aqueous solution containing about 3% to about 90% by weight $H_2O_2$.

6. The process of claim 1 wherein about 0.75 to about 2 moles of acetic acid are employed per mole of 2-halopyridine.

7. The process of claim 1 wherein about 0.1 to about 0.6 moles of catalyst are employed per mole of 2-halopyridine.

8. The process of claim 1 wherein said reacting step is carried out at a temperature from about 60° C. to about 85° C.

9. A method for producing a 2-halopyridine-N-oxide comprising reacting at a temperature from about 30° C. to about 120° C. (a) an aqueous solution containing from about 30% to about 70% by weight $H_2O_2$, (b) a 2-halopyridine selected from the group consisting of 2-chloropyridine and 2-bromopyridine, and (c) acetic acid in the presence of a catalyst selected from alkali metal bisulfates, ammonium bisulfate, and mixtures thereof in order to produce the corresponding 2-halopyridine-N-oxide; said reaction carried out by employing from about 0.75 to about 2.5 moles of $H_2O_2$ per mole of 2-halopyridine; employing from about 0.75 to about 2 moles of acetic acid per mole of 2-halopyridine; and employing from about 0.1 to about 0.6 moles of catalyst per mole of 2-halopyridine.

10. The method of claim 9 wherein said 2-halopyridine is 2-chloropyridine.

11. The method of claim 9 wherein said reaction temperature is from about 60° C. to about 85° C.

* * * * *

UNITED STATES PATENT AND TRADEMARK OFFICE
CERTIFICATE OF CORRECTION

PATENT NO. : 4,585,871

DATED : April 29, 1986

INVENTOR(S) : Max M. Boudakian

It is certified that error appears in the above-identified patent and that said Letters Patent is hereby corrected as shown below:

In column 2, line 44 delete "expensiVe" and insert --expensive--.

In column 3, line 7 delete "imited" and insert --limited--.

In column 4, line 30 delete "2-halopyridine." and insert --2-halopyridine-N-oxides.--.

In column 5, line 50 delete "ignificantly" and insert --significantly--.

In column 7, line 35 delete "NAHSO$_4$" and insert --NaHSO$_4$--.

In column 8, line 32 delete "MnO2" and insert --MnO$_2$--.

In column 10, line 51 delete "(1.0 mole, 113 6 gm)," and insert --(1.0 mole, 113.6 gm),--.

In column 11, line 14 delete "charge dhydrogen" and insert --charged hydrogen--.

In column 11, line 45 delete "1 561 moles" and insert --1.561 moles--.

In column 11, line 51 delete "pyridine-2-thio-N-oxide" and insert --pyridine-2-thiol-N-oxide--.

Signed and Sealed this

Sixteenth Day of September 1986

[SEAL]

Attest:

DONALD J. QUIGG

Attesting Officer

Commissioner of Patents and Trademarks